United States Patent [19]

Kulp et al.

[11] Patent Number: 4,630,378
[45] Date of Patent: Dec. 23, 1986

[54] GAUGE FOR EXTENSIBLE-BLADE SURGICAL KNIFE

[75] Inventors: Rodney J. Kulp, Harleysville; Andrew J. Furey, Philadelphia, both of Pa.

[73] Assignee: Pilling Co., Fort Washington, Pa.

[21] Appl. No.: 744,407

[22] Filed: Jun. 13, 1985

[51] Int. Cl.$^4$ ............................................. B27G 23/00
[52] U.S. Cl. .............................. 33/185 R; 33/180 R; 128/305
[58] Field of Search ............ 30/320; 33/169 B, 169 F, 33/169 R, 180 R, 185 R; 128/305

[56] References Cited

U.S. PATENT DOCUMENTS

| | | | |
|---|---|---|---|
| 3,323,221 | 6/1967 | Koch | 33/185 R |
| 4,473,076 | 9/1984 | Williams et al. | 128/305 |
| 4,499,898 | 2/1985 | Knepshield et al. | 128/305 |
| 4,538,356 | 9/1985 | Knepshield et al. | 33/185 R |

Primary Examiner—Stephen F. Husar
Attorney, Agent, or Firm—Howson and Howson

[57] ABSTRACT

A gauge for use in determining the extent to which the cutting blade of an extensible-blade keratotomy knife projects beyond the end of a cutting depth limiting foot, comprises a base, a knife-holding cradle slidable on the base, a clamping screw for clamping the cradle to the base in any selected position within a range, a block fixed to the base, and a gauge element slidable on the base and adjustably movable with respect to the block toward and away from the cradle. With a knife mounted on the cradle, and the gauge element at a predetermined reference position, the cradle is moved until the foot of the knife abuts one face of the gauge element. The gauge element is then moved away from the foot by an adjusting screw, until an edge of the gauge element underlies the tip of the knife blade. The top face of the gauge element and the base surface on which the gauge element slides are of contrasting colors. The cradle includes a post for supporting the knife body with a unitary spring wire hold-down clip pivoted on the post.

10 Claims, 6 Drawing Figures

GAUGE FOR EXTENSIBLE-BLADE SURGICAL KNIFE

BRIEF SUMMARY OF THE INVENTION

This invention relates to improvements in blade gauges for facilitating adjustment of the extent to which the blade tip of an extensible-blade surgical knife projects beyond the end of a cutting depth limiting foot attached to the body of the knife. The invention has particular utility in the adjustment of knives used in ophthalmological procedures such as radial keratotomy.

A typical keratotomy knife comprises a knife body, generally in the form of an elongated cylinder, containing a stem which is axially movable. A diamond blade is fixed at the end of the stem. The blade is at least partly surrounded by a foot, which serves not only to protect the blade, but also to limit the cutting depth. The limit of cutting depth is the extent to which the blade projects beyond the end of the foot. Axial positioning of the stem, and thus the extent to which the blade projects beyond the foot, is controlled by a screw mechanism within the knife body. Ordinarily, the control on the knife body for adjusting the position of the internal stem includes markings for providing an indirect indication of the cutting depth.

In radial keratotomy particularly, cutting depth is critical. Blade replacement, and interchange of parts can introduce errors into the indirect cutting depth indications provided by the knife itself. Accordingly, surgeons are reluctant to rely upon the indicator on the knife alone. They prefer to use a separate gauge which directly measures the extent to which the blade projects beyond the foot. The separate gauge can be used as an adjunct to the indicator on the knife itself, to confirm the readings given by the knife-carried indicator. Alternatively, the gauge can be used by itself as a setting device. In the latter case, the gauge is preset to the desired reading, and, with the knife in proper relationship to the gauge, the blade projection adjuster is operated until the blade reaches the desired position.

An example of a blade gauge used in conjunction with keratotomy knives appears in Knepshield et al. U.S. Pat. No. 4,499,898, issued Feb. 19, 1985. The Knepshield gauge comprises a gauge stand with knife-positioning elements engageable with a knife body to ensure proper positioning of the knife body with respect to the stand. A rotatable disc indicator, having a cylindrical exterior surface, is supported in a mounting slot on the gauge stand so that its cylindrical surface can be brought into abutment with the tip of the foot of the knife. The disc indicator is then clamped in place on the gauge stand by the tightening of a screw, but still allowed to rotate. The blade of the knife, projects beyond the cylindrical edge of the disc, and overlies the face of the disc. The face of the disc has a circle formed on it which is eccentric with respect to the cylindrical edge of the disc. Thus, the area between the eccentric circle and the edge of the disc varies in width. The disc is rotated until the eccentric circle is directly underneath the end of the knife blade, and the extent to which the knife blade projects beyond the end of the foot is determined from markings on the face of the disc, which may be read against the blade itself.

The present invention is an improvement over the gauge described in the Knepshield et al. patent.

The principal features of the invention include: a knife-support cradle which slides relative to a base; a gauge element which is initially in abutment with the end of the cutting depth limiting foot of the knife, but which moves away from the foot; contrasting colors on opposite sides of the edge of a gauge element; and a unitary wire hold-down clip for the knife body.

A preferred gauge in accordance with the invention comprises a base having guide means, a cradle slidably supported on the base and guided by the guide means, means on the cradle for holding the body of an extensible-blade surgical knife so that the cutting edge of the blade lies in a plane parallel to the direction of extension and retraction of the blade and fixed with respect to the cradle, and gauge means on the base comprising a gauge element having an edge located closely adjacent to said plane and substantially parallel thereto, said edge extending transverse to the direction of extension and retraction of the blade. The gauge element is capable of movement relative to the base parallel to said plane, through a range of positions including a reference position fixed with respect to the base, so that a projection of said edge onto the blade in a direction perpendicular to said plane, is movable in the direction of extension and retraction of the blade as the gauge element moves. Indicator means provide a reading of the position of said gauge element relative to the reference position. Means are provided for adjusting the position of the cradle on the base, thereby adjusting the location of the cradle relative to the reference position of the gauge element. Releasable means are provided for fixing the cradle with respect to the base, thereby fixing said location, while allowing said movement of the gauge element relative to the base.

Preferably, the gauge element is slidably supported on the base, and the gauge means also comprises a block fixed to the base, and thread means for adjustably moving the gauge element relative to the block in the direction of projection and retraction of the blade. The gauge element has a face extending from its edge in a direction perpendicular to the aforementioned plane in which the blade's cutting edge lies. This face is positioned to be abutted by the end of the cutting depth limiting foot of a knife held on the cradle so that, with the indicator means showing the gauge element at the reference position, the end of the foot can be brought into abutment with said face by operation of said means for adjusting the position of the cradle on the base. Thereafter, the face of the gauge element can be moved away from the foot by operation of said thread means to determine the extent to which the tip of the blade extends beyond the end of the foot.

The gauge element preferably has a second face extending from its edge in parallel to the aforementioned plane in which the cutting edge of the blade lies. The gauge element is slidable on a surface of the base which is also parallel to said plane. This second face of the gauge element and the surface on which the gauge element slides are of contrasting colors, so that the relationship of the tip of the knife blade to the edge of the gauge element can readily be determined visually.

Preferably, the cradle has an upwardly extending post having a top face with an arcuate recess for receiving the body of the knife, and also having front and rear faces extending transverse to the direction of elongation of the knife. Each of these front and rear faces has a hole for receiving the end of a spring wire clamping means used to hold the body of the knife in the arcuate recess.

The holes are aligned along a line parallel to the direction of elongation of the knife. The clamping means comprises a unitary length of spring wire having its ends respectively located in the holes in the front and rear faces of the post, whereby the clamping means can pivot about said line. The length of spring wire comprises a first inverted J-shaped section located substantially in a first plane on the rear side of the post and a second inverted J-shaped section located substantially in a second plane on the front side of the post. The first and second planes are parallel to each other and transverse to the direction of elongation of the knife. Each of the J-shaped sections comprises a leg and an arcuate section. Each leg connects one of the ends of the wire to one end of an arcuate section. The clamping means also comprises a connecting section extending substantially parallel to the direction of elongation of the knife and connecting together the ends of the two arcuate sections which are remote from the legs. The clamping means is shaped so that its spring characteristic holds its ends in the holes in the front and rear faces of the post, and so that the arcuate sections are capable of overlying a knife body located in the recess and holding the knife body in place in the recess. The J-shaped sections are shaped, and the holes are positioned, so that an imaginary line extending from one end of each J-shaped section to the other end of the same section is located substantially below the center of the arc of the arcuate recess when the clamping means is holding the knife body in the recess.

The principal object of the present invention is to provide an improved blade gauge which is more accurate, more versatile, and easier to use than the gauge described in the Knepshield et al. patent. The manner in which this object is accomplished and various further objects and advantages of the invention will be apparent from the following detailed description when read in conjunction with the drawings.

DETAILED DESCRIPTION

Figure 1:
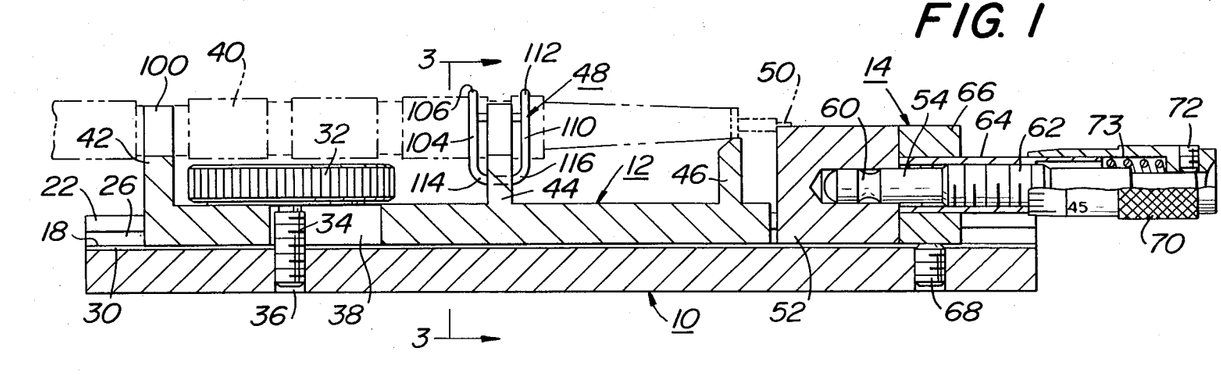
FIG. 1 is a section taken on a vertical plane extending longitudinally through a gauge in accordance with the invention, with a keratotomy knife shown in broken lines.
Figure 2:
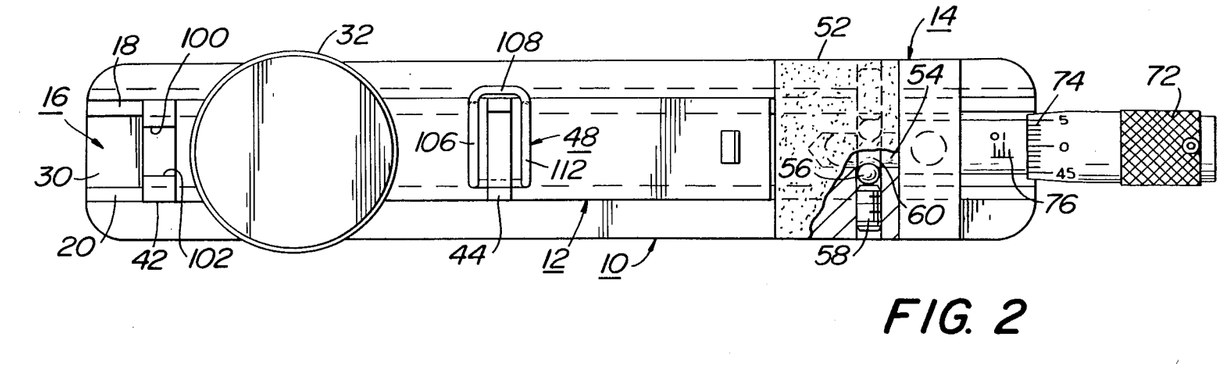
FIG. 2 is a top plan view of the gauge, partially broken away to show the manner in which an adjusting stem is held by balls in a movable gauge element.

As shown in FIGS. 1 and 2, the gauge of the invention comprises a base 10, a knife-supporting cradle 12, and gauge means 14.

A channel 16, best shown in FIG. 2, extends lengthwise along the top of the base from one end to the other. Cradle 12 is supported by horizontal surfaces 18 and 20 within the channel, and is slidable thereon.

Figures 3, 4:
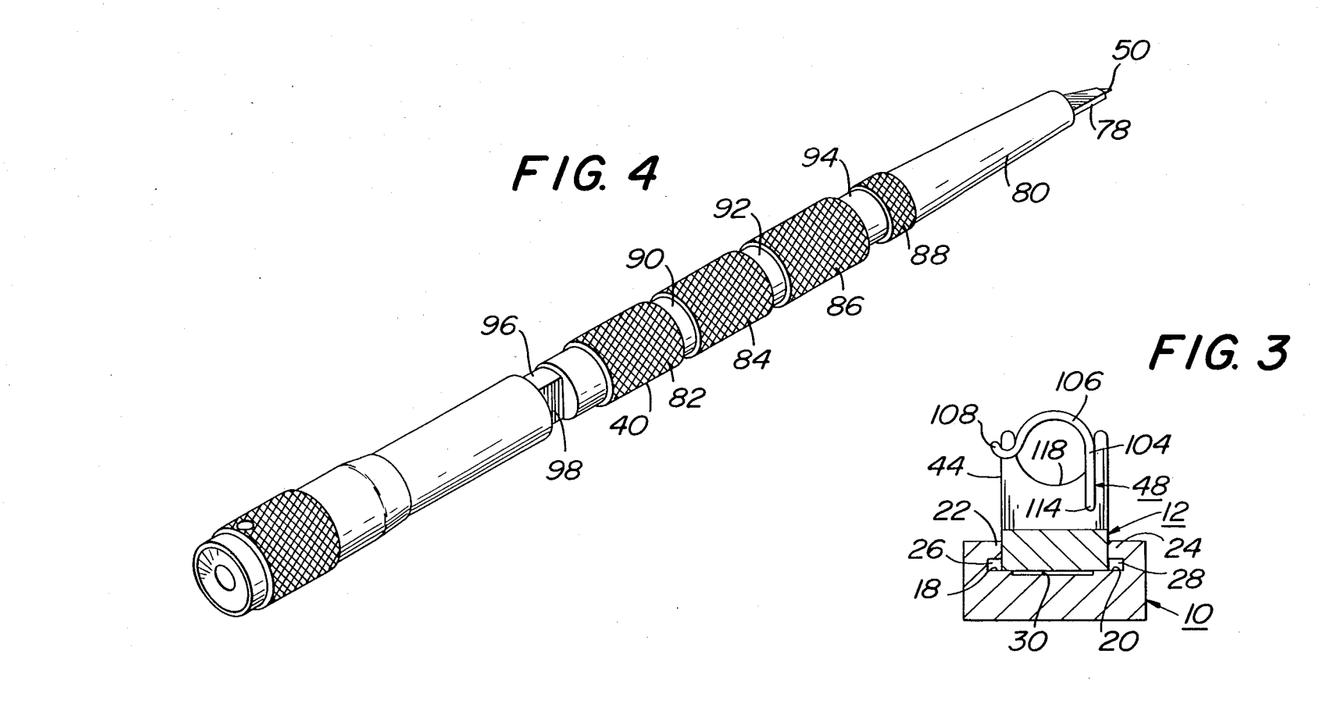
FIG. 3 is a vertical section taken on plane 3—3 in FIG. 1.
FIG. 4 is a perspective view of a typical keratotomy knife with which the gauge is used.

As shown in FIG. 3, base 10 has overhanging elements 22 and 24 which engage the sides of cradle 12, guiding it by constraining it against horizontal movement in directions other than along the length of the channel. Slots 26 and 28 are found respectively underneath overhanging parts 22 and 24. These slots are used to fix a part of gauge means 14 to the base, as will be described.

The floor of channel 16 is also provided with a recess 30 located between cradle support surfaces 18 and 20. Recess 30 facilitates tightening of the cradle against surfaces 18 and 20 by a clamp which comprises knurled wheel 32, and a threaded stem 34 which is threaded into hole 36 in the base, as shown in FIG. 1. Threaded stem 34 extends through a slot 38 in the cradle. When the clamp is tightened, the underside of wheel 32 bears against the upper surface of the cradle, fixing the cradle with respect to the base. When the clamp is loosened, slot 38 allows a limited longitudinal movement of the cradle in channel 16.

A knife 40 is held on the cradle by support pedestals 42, 44 and 46. The knife is held down by wire clamp 48 on pedestal 44.

The knife is positioned so that its blade 50, when extended, is located just above the level of the upper surface of a movable gauge element 52. The gauge element is slidable longitudinally on the base, and is guided in channel 16. Blade 50 can extend over gauge element 52 in close proximity to the top surface of the gauge element, as shown in FIG. 1. The gauge element is secured to an adjusting stem 54 by a ball bearing 50 and a set screw 58, as shown in FIG. 2. Set screw 58 holds ball 56 in groove 60 on stem 54. Another ball is similarly held in groove 60 on the opposite side of the stem. Threads 62 on stem 54 are engaged with internal threads in a barrel 64, which is fixed to, and extends outwardly from, block 66. Block 66 has feet (not shown) which fit into slots 26 and 28 (FIG. 3) underneath overhanging parts 22 and 24. The block is urged upwardly against overhanging parts 22 and 24 by set screw 68 (FIG. 1), and thereby held securely in a fixed position with respect to base 10. A knurled micrometer barrel 70 is secured to stem 54 by a set screw 72. The micrometer barrel 70 is hollow, and barrel 64 extends partway into the end of the barrel 70. A compression spring 73 bears against the end of barrel 64, and urges the micrometer barrel outwardly, thereby eliminating play between threads 62 and the mating threads on the interior surface of barrel 64.

As shown in FIG. 2, markings 74 on the micrometer barrel, when read in conjunction with markings 76 on the exterior of barrel 64, provide an indication of the position of gauge element 52 relative to block 66.

In FIGS. 1 and 2, gauge element 52 is shown positioned against a face of block 66. When the edge of barrel 72 is aligned with the zero marking on barrel 64, gauge element 52 will be separated from block 66. In operation, the gauge element is moved toward the block by counterclockwise rotation of micrometer barrel 72.

The keratotomy knife shown in FIG. 4 has a cutting depth limiting foot 78 surrounding the blade 50. The extent to which the blade projects beyond the end of foot 78 is adjustable by suitable adjusting means within the knife body.

A tapered section 80 extends from foot 78 toward a series of knurled sections 82, 84, 86 and 88. The knurled sections are separated by gaps 90, 92 and 94. Beyond knurled section 82, there is provided a reduced section 96 having flat faces, one of which is seen at 98. These flat faces are perpendicular to the plane in which the knife blade lies, and cooperate with vertical faces 100 and 102 (FIG. 2) of pedestal 44 to prevent rotation of the knife, and thereby hold the knife blade in parallel relation to the upper face of gauge element 52.

As shown in FIG. 1, pedestal 46 engages the end of the tapered section of the knife body, and is of a height such that it positions the knife blade in very close proximity to the upper face of gauge element 52 while preventing contact between the blade and the gauge element.

Referring now to FIGS. 1 and 3, wire clamp 48 on intermediate pedestal 44 comprises a first vertical section 104, an arcuate section 106, a horizontal connecting section 108 (FIG. 2), a second vertical section 110, and a second arcuate section 112. The connecting section 108 connects the ends of arcuate sections 106 and 112. Vertical sections 104 and 110 extend downwardly along the sides of pedestal 44, and terminate in horizontal sections 114 and 116 respectively, which extend into opposite ends of a through hole in the pedestal. The wire clamp is pivotable in the through hole.

When section 94 (FIG. 4) of the knife is positioned in semi-circular trough 118 of pedestal 48 (FIG. 3), the wire clamp is positioned over knurled parts 86 and 88 of the knife body. Because of its spring characteristic, the wire clamp holds the knife securely in place, thereby reducing the likelihood of accidental damage to the blade.

Referring to FIG. 3, the lower ends of the straight sections of the wire clamp 48 are positioned well below the trough 118 so that if an imaginary line were to be drawn from the end of arcuate section 106 remote from section 104 to end 114, there is a point on the imaginary line directly below, and a substantial distance below, the center of the arc of recess 118. This insures that the wire clamp will not accidentially swing out of its clamping position, but at the same time allows it to be manually engaged with, and disengaged from, the knife body by manipulation of connecting section 108 to deform the spring clamp slightly.

Figure 5:
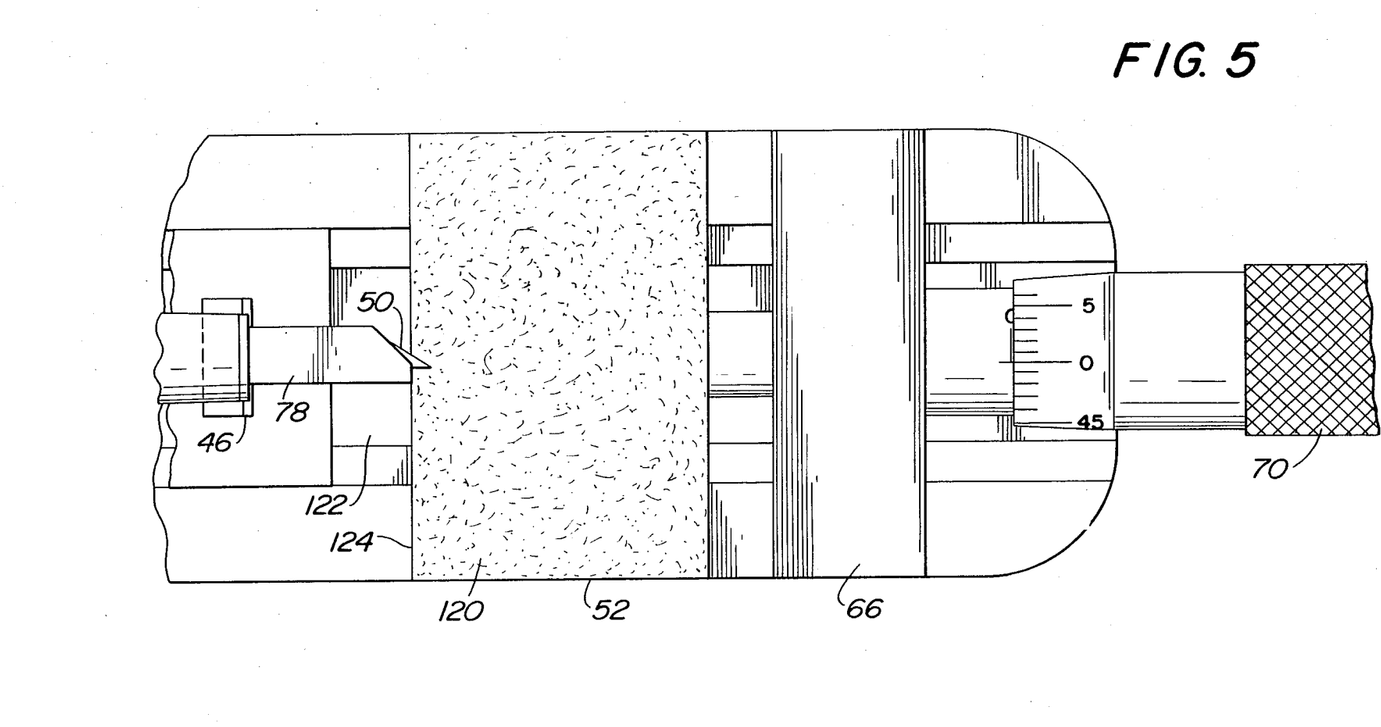
FIG. 5 is a fragmentary top plan view showing the gauge element at a reference position, with its face in contact with the foot of a keratotomy knife.

Referring to FIG. 5, which shows gauge element 52 separated from fixed gauge block 66, vertical face 124 of gauge element 52 is in contact with the end of cutting depth limiting foot 78. Knife blade 50 overlies planar top surface 120 of gauge element 52. This top surface and surface 122 of recess 30 in the face of the channel are of contrasting colors, providing a high degree of visibility for the knife blade. Preferably, the parts are made of aluminum. Gauge element 52 is anodized and dyed black. Surface 122 is also anodized, but preferably remains in the ordinary undyed aluminum color.

Figure 6:
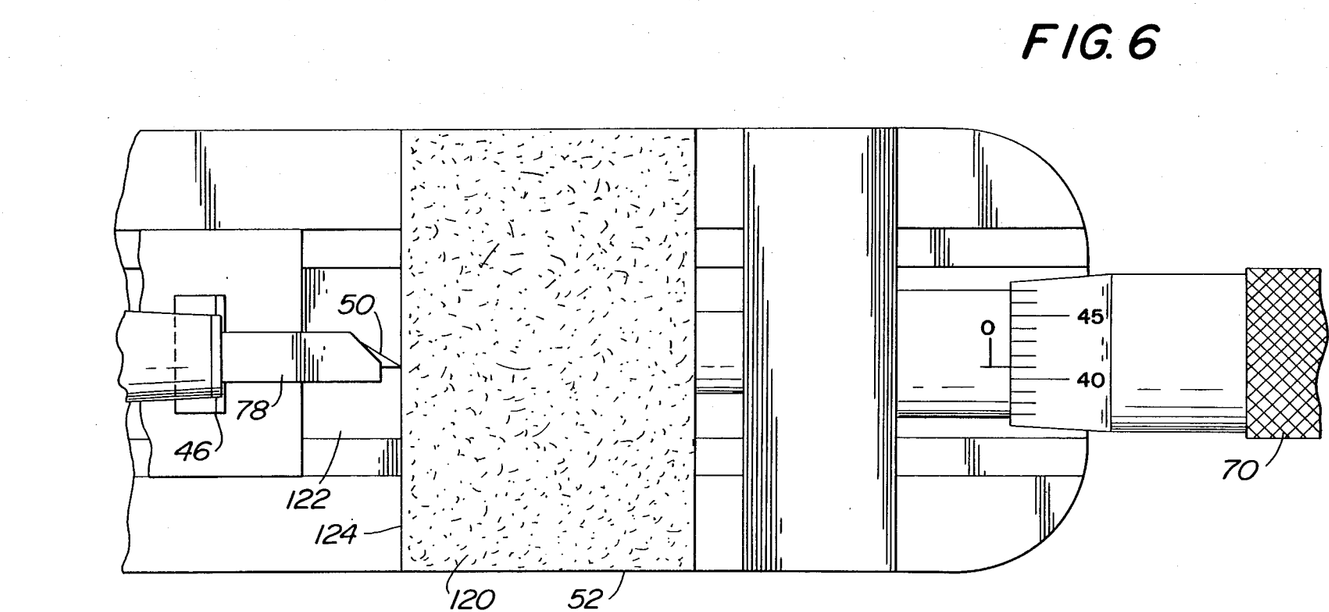
FIG. 6 is a fragmentary top plan view showing the gauge element moved away from the foot of the keratotomy knife and positioned directly underneath the tip of the knife blade.

In FIG. 6, gauge element 52 is shown with its face 124 separated from the cutting depth limiting foot, and with the edge at which surface 120 meets face 124 directly underneath the tip of the knife blade. The contrasting colors of surfaces 120 and 122 allow the relationship between this edge and the tip of the knife blade to be determined accurately so that the extent to which the blade projects beyond the end of the foot can be read from the markings associated with adjusting micrometer barrel 70. Typically, the knife blade is viewed through a low-power magnifier. The knife blade is maintained very close to the plane of gauge element surface 120 to minimize the effect of parallax.

The gauge is normally used to aid the surgeon in setting a knife to a desired cutting depth. The procedure for setting the knife normally begins with the blade 50 fully retracted into foot 78. The cradle is first moved away from the gauge element, and the knife is placed on the cradle and secured by spring clamp 48. The gauge means is brought to the "zero" or reference position depicted in FIG. 5 by adjustment of micrometer barrel 70. The cradle is then moved along channel 16 until the end of the cutting depth limiting foot 78 engages face 124 of gauge element 52, as shown in FIG. 5. The blade, however, is not extended at this time. The cradle is locked into position relative to base 10 by means of clamp 32. The micrometer barrel 70 is rotated counter-clockwise until its markings indicate the desired cutting depth. This rotation of the micrometer barrel causes the gauge element to back away from the foot by a distance equal to the desired cutting depth. The knife blade is then extended while the relationship between the tip of the blade and the gauge element is observed through a magnifier. When the tip of the blade reaches the edge of the gauge element, the knife is adjusted to the desired cutting depth.

While the gauge can be used, in the manner just described, to aid in adjusting the knife, it can also be used to measure the extent to which an already extended blade projects beyond the foot. To accomplish this, the gauge element is brought to the "zero" position, the knife is clamped in place on the cradle, and the cradle is moved toward the gauge element until the foot abuts gauge element face 124 as shown in FIG. 5. The knife blade overlies top surface 120 of the gauge element at this time. The cradle is then locked to the base, and the gauge element is backed away from the front until the edge of the gauge element is directly underneath the tip of the blade as shown in FIG. 6. The cutting depth can then be read directly from the markings on the micrometer barrel.

The knife itself will normally have its own markings, and the indications given by the markings on the knife will be confirmed by the indications provided by the gauge in either mode of operation. Confirmation is particularly important in radial keratotomy, because cutting depth is critical, and the indicator on the knife itself provides only an indirect indication of cutting depth, and may be in error due to wear, blade breakage, or improper blade installation.

The gauge has the particular advantage that it allows accurate measurement of the extent to which a knife blade projects beyond its foot throughout a range from zero cutting depth to well beyond the maximum usable cutting depth. Because this range extends all the way to zero cutting depth, a knife can be calibrated against the gauge throughout the entire range of cutting depths. The ability to calibrate an adjustable knife in this way greatly contributes to the surgeon's confidence in the indirect cutting depth indications given by the knife itself.

The gauge provides accurate and easily readable indications of cutting depth. It also has the advantage that its cradle can be easily replaced by removal of clamp 32 so that the same base and gauge means can be used with a variety of different cradles adapted for different styles of knives.

As mentioned previously, the invention also has the advantage that the wire clamp securely holds the knife in the cradle, thereby greatly reducing the likelihood of breakage of the knife blade by dropping the knife.

Finally, improved accuracy is achieved by the contrast between the gauge element and the surface adjacent to the gauge element.

Various modifications can be made to the invention described. For example, while the gauge element preferably moves parallel to the knife axis, this is not necessarily the case. Fine adjustment of the gauge element can be achieved without the micrometer assembly shown in the drawings, by adoption of a wedge-shaped gauge element movable along a surface which is oblique in plan view with respect to the knife axis. By using a wedge, a relatively large amount of movement of the gauge element in the oblique direction will result in a relatively small, but accurately determinable movement of the projection of the edge of the gauge element onto the knife blade. Consequently, accurate readings can be obtained. Many other modifications may, of course, be made to the invention herein described without departing from its scope as defined by the following claims.

I claim:

1. A gauge for facilitating adjustment of the extent to which the blade tip of an extensible-blade surgical knife projects beyond the end of a cutting depth limiting foot attached to the body of the knife comprising:

a base having guide means;

a cradle slidably supported on said base and guided by said guide means;

means on the cradle for holding the body of an extensible-blade surgical knife so that the cutting edge of the blade lies in a plane parallel to the direction of extension and retraction of the blade and fixed with respect to the cradle;

gauge means on said base comprising a gauge element having an edge located closely adjacent to said plane and substantially parallel thereto, said edge extending transverse to the direction of extension and retraction of the blade, said gauge element being capable of movement relative to the base parallel to said plane, through a range of positions including a reference position fixed with respect to the base, so that a projection of said edge onto the blade, in a direction perpendicular to said plane, is movable in the direction of extension and retraction of the blade as the gauge element moves, and indicator means providing a reading of the position of said gauge element relative to the reference position; and releasable means for fixing the cradle with respect to the base, thereby fixing the location of the cradle relative to said reference position of the gauge element while allowing said movement of the gauge element relative to the base.

2. A gauge according to claim 1 in which said gauge element is slidably supported on said base, and in which said gauge means comprises a block fixed to the base, and thread means for adjustably moving said gauge element relative to the block in the direction of extension and retraction of the blade, the gauge element having a face extending from said edge in a direction perpendicular to said plane and being positioned to be abutted by the end of the cutting depth limiting foot of a knife held on the cradle, whereby, with the indicator means showing the gauge element at the reference position, the end of said foot can be brought into abutment with said face, the cradle can be fixed to the base by said releasable means, and thereafter the face of the gauge element can be moved away from the foot by operation of said thread means to determine the extent to which the blade tip extends beyond the end of the foot.

3. A gauge according to claim 2 in which the gauge element has a second face extending from said edge of the gauge element in parallel to said plane in which the cutting edge of the blade lies, in which the gauge element is slidable on a surface of said base, said surface also being parallel to said plane, and in which said second face and said surface are of contrasting colors, whereby the relationship of the tip of the knife blade to the edge of the gauge element can readily be determined visually.

4. A gauge according to claim 1 in which said means on the cradle for holding the body of an extensible-blade surgical knife comprises a post extending upwardly from the cradle, the post having a top face with an arcuate recess for receiving the body of the knife and also having front and rear faces extending transverse to the direction of elongation of the knife, each of the front and rear faces having a hole for receiving the end of a spring wire clamping means, the holes being aligned along a line parallel to the direction of elongation of the knife, and clamping means for holding the body of the knife in the arcuate recess, the clamping means comprising a unitary length of spring wire having its ends respectively located in the holes in the front and rear faces of the post whereby the clamping means can pivot about said line, the length of spring wire comprising a first J-shaped section located substantially in a first plane on the rear side of the post and a second J-shaped section located substantially in a second plane on the front side of the post, said first and second planes being parallel to each other and transverse to the direction of elongation of the knife, and each of the J-shaped sections comprising a leg and an arcuate section, the leg connecting one of said ends to one end of the arcuate section, and the clamping means also comprising a connecting section extending substantially parallel to the direction of elongation of the knife and connecting together the ends of the two arcuate sections which are remote from the legs, the clamping means being shaped so that its spring characteristic holds its ends in said holes in the front and rear faces of the post, and so that the arcuate sections are capable of overlying a knife body located in said recess and holding said knife body in place in said recess, and said J-shaped sections being shaped and said holes being positioned so that an imaginary line extending from one end of each J-shaped section to the other end of the same section is located substantially below the center of the arc of said arcuate recess when the clamping means is holding said knife body in said recess.

5. A gauge for facilitating adjustment of the extent to which the blade tip of an extensible-blade surgical knife projects beyond the end of a cutting depth limiting foot attached to the body of the knife comprising:

a cradle;

means on the cradle for holding the body of an extensible-blade surgical knife so that the cutting edge of the blade lies in a plane parallel to the direction of extension and retraction of the blade and fixed with respect to the cradle;

gauge means comprising a gauge element having an edge located closely adjacent to said plane and substantially parallel thereto, said edge extending transverse to the direction of extension and retraction of the blade, said gauge element being capable of movement relative to the cradle parallel to said plane, through a range of positions including a reference position, so that a projection of said edge onto the blade, in a direction perpendicular to said plane, is movable in the direction of extension and retraction of the blade as the gauge element moves, and indicator means providing a reading of the position of said gauge element relative to the reference position;

means for adjusting the location of the cradle relative to the reference position of the gauge element; and releasable means for fixing said location while allowing said movement of the gauge element;

said gauge means comprising a block, and thread means for adjustably moving said gauge element relative to the block in the direction of extension and retraction of the blade, said releasable means fixing the location of the cradle relative to the block, the gauge element having a face extending from said edge in a direction perpendicular to said plane and being positioned to be abutted by the end of the cutting depth limiting foot of a knife held on the cradle;

whereby, with the indicator means showing the gauge element at the reference position, the end of said foot can be brought into abutment with said face by operation of said means for adjusting the location of the reference position, the location of the cradle relative to the reference position can be fixed by said releasable means, and thereafter the face of the gauge element be moved away from the foot by operation of said thread means, to determine the extent to which the cutting blade tip projects beyond the end of the foot.

6. A gauge according to claim 5 in which the gauge element has a second face extending from said edge of the gauge element in parallel to said plane in which the cutting edge of the blade lies, and having means providing a surface, parallel to said plane, and on which the gauge element is slidable, said second face and said surface being of contrasting colors, whereby the relationship of the tip of the knife blade to the edge of the gauge element can readily be determined visually.

7. A gauge for facilitating adjustment of the extent to which the blade tip of an extensible-blade surgical knife projects beyond the end of a cutting depth limiting foot attached to the body of the knife comprising:

a cradle;

means on the cradle for holding the body of an extensible-blade surgical knife so that the cutting edge of the blade lies in a plane parallel to the direction of extension and retraction of the blade and fixed with respect to the cradle;

gauge means comprising a gauge element having an edge located closely adjacent to said plane and substantially parallel thereto, said edge extending transverse to the direction of extension and retraction of the blade, said gauge element being capable of movement relative to the cradle parallel to said plane, through a range of positions including a reference position, so that a projection of said edge onto the blade, in a direction perpendicular to said plane, is movable in the direction of extension and retraction of the blade as the gauge element moves, and indicator means providing a reading of the position of said gauge element relative to the reference position;

means for adjusting the location of the cradle relative to the reference position of the gauge element; and releasable means for fixing said location while allowing said movement of the gauge element;

the gauge having surfaces viewable through said plane, on both sides of said edge, the surfaces being of contrasting colors whereby the relationship of the cutting edge of the knife blade to the edge of the gauge element can readily be determined visually.

8. A gauge according to claim 7 in which the gauge comprises a first surface parallel to said plane in which the cutting edge of the blade lies, in which the gauge element has a second surface also parallel to said plane and extending from said edge of the gauge element, said gauge element being slidable over said first surface, and said surfaces of contrasting colors being said first and second surfaces.

9. A gauge for facilitating adjustment of the extent to which the blade tip of an elongated extensible-blade surgical knife projects beyond the end of a cutting depth limiting foot attached to the body of the knife comprising:

a cradle;

means on the cradle for holding the body of an extensible-blade surgical knife so that the cutting edge of the blade lies in a plane parallel to the direction of extension and retraction of the blade and fixed with respect to the cradle;

gauge means comprising a gauge element having an edge located closely adjacent to said plane and substantially parallel thereto, said edge extending transverse to the direction of extension and retraction of the blade, said gauge element being capable of movement relative to the cradle parallel to said plane, through a range of positions including a reference position, so that a projection of said edge onto the blade, in a direction perpendicular to said plane, is movable in the direction of extension and retraction of the blade as the gauge element moves, and indicator means providing a reading of the position of said gauge element relative to the reference position;

means for adjusting the location of the cradle relative to the reference position of the gauge element; and releasable means for fixing said location while allowing said movement of the gauge element;

said means on the cradle for holding the body of an extensible-blade surgical knife comprising a post extending upwardly from the cradle, the post having a top face with an arcuate recess for receiving the body of the knife and also having front and rear faces extending transverse to the direction of elongation of the knife, each of the front and rear faces having a hole for receiving the end of a spring wire clamping means, the holes being aligned along a line parallel to the direction of elongation of the knife, and clamping means for holding the body of the knife in the arcuate recess, the clamping means comprising a unitary length of spring wire having its ends respectively located in the holes in the front and rear faces of the post whereby the clamping means can pivot about said line, the length of spring wire comprising a first J-shaped section located substantially in a first plane on the rear side of the post and a second J-shaped section located substantially in a second plane on the front side of the post, said first and second planes being parallel to each other and transverse to the direction of elongation of the knife, and each of the J-shaped sections comprising a leg and an arcuate section, the leg connecting one of said ends to one end of the arcuate section, and the clamping means also comprising a connecting section extending substantially parallel to the direction of elongation of the knife and connecting together the ends of the two arcuate sections which are remote from the legs, the clamping means being shaped so that its spring characteristic holds its ends in said holes in the front and rear faces of the post, and so that the arcuate sections are capable of overlying a knife body located in said recess and holding said knife body in place in said recess, and said J-shaped sections being shaped and said holes being positioned so that an imaginary line extending from one end of each J-shaped section to the other end of the same section is located substantially below the center of the arc of said arcuate recess when the clamping means is holding said knife body in said recess.

10. A gauge according to claim 9 in which said aligned holes in the front and rear faces of the post are located below the level of the lowermost point in said arcuate recess.

* * * * *